US006284545B1

(12) United States Patent
Warburton et al.

(10) Patent No.: US 6,284,545 B1
(45) Date of Patent: Sep. 4, 2001

(54) FILTER FOR GAS SENSOR

(75) Inventors: P. Richard Warburton, Moon Township; Ronald Scott Sawtelle, Indiana, both of PA (US)

(73) Assignee: Industrial Scientific Corporation, Oakdale, CA (US)

( * ) Notice: Subject to any disclaimer, the term of this patent is extended or adjusted under 35 U.S.C. 154(b) by 0 days.

(21) Appl. No.: 09/275,040

(22) Filed: Mar. 24, 1999

(51) Int. Cl.$^7$ .................................................. G01N 27/26
(52) U.S. Cl. ........................... 436/124; 436/127; 436/153; 436/806; 422/50; 422/83; 422/88; 422/90; 422/98
(58) Field of Search .................. 422/50, 83, 88, 422/90, 98; 436/153, 124, 127, 806

(56) References Cited

U.S. PATENT DOCUMENTS

| | | | |
|---|---|---|---|
| 3,909,384 | * | 9/1975 | Jasinski et al. .................. 204/195 G |
| 4,001,103 | * | 1/1977 | Blurton et al. ................... 204/195 R |
| 4,141,800 | * | 2/1979 | Breuer et al. .......................... 204/1 T |
| 4,472,247 | * | 9/1984 | Rohr et al. ............................ 204/1 T |
| 4,911,892 | * | 3/1990 | Grace et al. ............................ 422/94 |
| 5,502,308 | * | 3/1996 | Wong ................................. 250/338.5 |
| 5,624,546 | * | 4/1997 | Milco ................................. 205/779.5 |

FOREIGN PATENT DOCUMENTS

02024552 A * 1/1990 (JP) .
3016407 B2 * 3/2000 (JP) .

* cited by examiner

Primary Examiner—Jill Warden
Assistant Examiner—Yelena Gakh
(74) Attorney, Agent, or Firm—Dennison, Scheiner, Schultz & Wakeman

(57) ABSTRACT

A filter for reducing the cross-sensitivity of a chlorine dioxide detector to hydrogen sulfide. The filter includes a high surface area substrate impregnated with a silver (I) salt or copper (II) salt which is effective to remove hydrogen sulfide from a gas stream without producing undesirable compounds which might be detected by the sensor. The preferred compounds are copper chloride ($CuCl_2$), copper bromide ($CuBr_2$), silver acetate ($AgO_2CCH_3$), silver bromate ($AgBrO_3$), silver bromide ($AgBr$), silver carbonate ($Ag_2CO_3$), silver chloride ($AgCl$), silver chromate ($Ag_2CrO_4$), silver cyanide ($AgCN$), silver iodate ($AgIO_3$), silver oxide ($Ag_2O$), silver perchlorate ($AgClO_4$), silver permanganate ($AgMnO_4$), silver sulfate ($Ag_2SO_4$), silver hexafluorophosphate ($AgPF_6$), silver fluoride ($AgF$), silver tetrafluoroborate ($AgBF_4$), silver iodide ($AgI$) and silver trifluoromethane sulfonate ($AgO_3SCF_3$).

13 Claims, 2 Drawing Sheets

FILTER FOR GAS SENSOR

BACKGROUND OF THE INVENTION

Chlorine dioxide ($ClO_2$) is a highly reactive gas that is used as a substitute for chlorine, which is rapidly being phased out of many industries, such as pulp and paper, flour and textiles, due to environmental concerns regarding the formation of dioxins. In addition to being used as a bleaching agent, chlorine dioxide is also used for other purposes such as the disinfection and sterilization of foods and drinking water, and for the treatment of leather. Chlorine dioxide is so highly reactive that it cannot easily be stored in compressed gas cylinders, and must be generated at the point of use. Chlorine dioxide is commonly generated by the electrochemical oxidation of chlorite salts. Further details of the chemistry of chlorine dioxide may be found in standard texts, such as "Chlorine Dioxide—Chemistry and Environmental Impact of Oxychlorine Compounds," W. J. Masschelein, Ann Arbor Science Publishers Inc, Ann Arbor, Mich.

This high level of reactivity is also reflected in a high toxicity, and the OSHA work place permissible exposure to chlorine dioxide is only 0.1 ppm averaged over an eight hour shift, with a level of 5 ppm considered immediately dangerous to life and health (NIOSH Pocket Guide to Chemical Hazards, U.S. Department of Health and Human Services, June 1997). Thus, it is important to have adequate protection of personnel who are using chlorine dioxide. While most facilities using chlorine dioxide gas use engineering controls to ensure that the ambient concentration of chlorine dioxide is maintained at safe levels, leaks and other emissions unfortunately do occur, posing a risk to personnel in the vicinity. Therefore, it is common practice to use gas detection instruments to monitor for chlorine dioxide and other potentially hazardous gases.

These instruments may be portable instruments intended to provide personal protection, and are typically worn by the personnel to be protected. Alternatively, fixed (e.g. wall mounted) gas detection devices may be employed which monitor the area for the presence of potentially hazardous atmospheres. In a typical application such as a paper mill, instruments may be used to detect chlorine dioxide, hydrogen sulfide, sulfur dioxide and oxygen deficiency. In many cases, multi-gas instruments are available which incorporate sensors for several different types of gases.

Hydrogen sulfide is typically found in many industrial applications, including petroleum-refining operations, coking of coal, purification of natural gas and the evaporation of black liquor in Kraft pulping. For large-scale operations, the hydrogen sulfide is recovered and converted to sulfur dioxide for subsequent conversion to sulfuric acid or elemental sulfur. For smaller scale operations, other pollution control processes are used, such as iron-oxide fire boxes, wet scrubbers containing solutions of oxidants such as chlorine, alkaline potassium permanganate or atmospheric oxygen, or bases such as organic amines, (e.g. ethanolamine) and tripotassium phosphate and sodium carbonate ("Industrial Pollution control Handbook", H. F. Lund, Ed., McGraw-Hill book Company, New York, 1971; "Pollutant Removal Handbook", M. Sittig, Noyes Data Corporation, Park Ridge, N.Y., 1973; Kirk-Othmer Encyclopedia of Chemical Technology, 2nd Ed., Vol. 19, Interscience Publishers, New York, 1969). More recently, a number of cobalt, iron and manganese chelate and macrocycle compounds have also been used to catalyze the air oxidation of hydrogen sulfide. Mimoun et al in U.S. Pat. No. 3,956,473 and Deberry et al in U.S. Pat. No. 5,705,135, describe the use of iron chelates in non-aqueous solvents. Anderson et al in U.S. Pat. No. 3,923,645 describe the use of substituted cobalt porphyrins as catalysts for the air oxidation of hydrogen sulfide. Analogously, Verachtert in U.S. Pat. No. 5,244,643 describes the use of transition metal phthalocyanine complexes as catalysts for the air oxidation of hydrogen sulfide and mercaptans in aqueous alkali. Bridges et al in U.S. Pat. No. 5,527,517 have also described the removal of hydrogen sulfide from a gas stream by oxidation of the hydrogen sulfide by aqueous hydrogen peroxide, catalyzed by a silver nitrate or other silver salts.

Hydrogen sulfide gas is of particular concern in those locations where both hydrogen sulfide and chlorine dioxide may be found. Typical locations include pulp and paper mills, water treatment plants, etc. Hydrogen sulfide is a toxic gas, the OSHA permissible exposure limit having a ceiling value of 10 ppm and a level considered immediately dangerous to life and health (IDLH) of 100 ppm (NIOSH Pocket Guide to Chemical Hazards, U.S. Department of Health and Human Services, June 1997). Thus, although hydrogen sulfide is a highly toxic gas, it is less toxic than chlorine dioxide.

In electrochemical gas sensors, the response to hydrogen sulfide is typically the eight-electron oxidation hydrogen sulfide to sulfuric acid.

$$H_2S+4H_2O \rightarrow H_2SO_4+8H^++8e^-$$

The response of an electrochemical sensor to chlorine dioxide is typically either the one electron reduction to hydrogen chlorite:

$$ClO_2+H^++e^- \rightarrow HClO_2$$

or the five electron reduction to chloride ion:

$$ClO_2+4H^++5e^- \rightarrow 2H_2O+Cl^-$$

depending on the electrodes and electrolytes used in the sensor. Since hydrogen sulfide is less toxic than chlorine dioxide, a concentration of hydrogen sulfide, within the permissible exposure levels, maybe larger than the permissible exposure levels for chlorine dioxide. Furthermore, the hydrogen sulfide will give a much larger response from the electrochemical gas sensor per unit concentration (eight electrons for hydrogen sulfide versus one electron for chlorine dioxide).

In view of the ease with which hydrogen sulfide is oxidized, electrochemical sensors are often designed to have a reduced sensitivity to hydrogen sulfide compared to the response expected based on gas diffusion of hydrogen sulfide. Despite the efforts of sensor designers, there is still usually a significant response from the sensors to hydrogen sulfide.

However, the most serious problem from a safety perspective is that the response to hydrogen sulfide in an electrochemical sensor is an oxidation reaction, whereas the response to chlorine dioxide in an electrochemical sensor is a reduction reaction. Exposure of a chlorine dioxide detection instrument to hydrogen sulfide alone will usually give a negative response. The response to hydrogen sulfide is in the opposite polarity to the response to chlorine dioxide, and thus the sum of the responses of chlorine dioxide and hydrogen sulfide will be less than that of the same concentration of chlorine dioxide on its own.

Hydrogen sulfide also responds on other electrochemical gas sensors; unfiltered sensors for carbon monoxide, sulfur dioxide, nitrogen dioxide, chlorine, hydrogen, hydrogen chloride and ammonia from, for example, City Technology Ltd., one of the largest gas sensor manufacturers, all give a responses to hydrogen sulfide (Product Data Handbook, Vol. 1. Issue 4, Safety, City Technology Ltd., Portsmouth, United Kingdom, June 1997).

Many sensors incorporate chemical filters in an attempt to reduce the cross sensitivity to hydrogen sulfide; however chemical filters cannot be used for all types of gas sensors, since the filter must scrub out the unwanted gas, but still let the analyte gas pass through to the sensor electrodes. The use of chemical filters within sensors is well known in the prior art; for example, Tantam and Chan in U.S. Pat. No. 4,633,704 describe the use of a soda lime filter to prevent hydrogen sulfide from giving a response on a carbon monoxide sensor.

Carbon filters are also commonly used to protect gas sensors from hydrogen sulfide, as is illustrated by Kiesele et al in U.S. Pat. No. 5,865,973, Xu in U.S. Pat. No. 5,803,337 and Martell et al in U.S. Pat. No. 5,744,697. The use of carbon filters is restricted to only a few types of gas sensors, since activated carbon absorbs a wide range of gases.

One common type of filter employs an oxidizing agent, such as potassium permanganate. Commercially available potassium permanganate impregnated filter media for air filtration are available from companies such a Purafil Inc., Doraville, Ga. Potassium permanganate is a strong oxidizing agent, and oxidizes any hydrogen sulfide which comes into contact with the filter medium, thus preventing it from entering the sensor. Since potassium permanganate is such a strong oxidizing agent, it will remove most easily oxidizable gases, including chlorine dioxide. Thus it is only suitable for relatively few types of gas sensors, such as those for carbon monoxide.

Chlorine commonly exists in oxidation states from −1 to +7, so chlorine dioxide, with chlorine in oxidation state +4 can be both oxidized and reduced, as is illustrated by the following redox reactions (CRC Handbook of Chemistry and Physics, 68$^{th}$ Edition, 1987–1988, R. C. Weast, M. J. Astle, W. H. Beyer, Eds.):

Reduction: 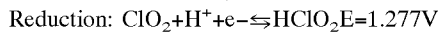

Oxidation: 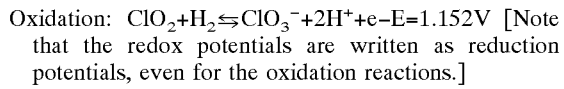 [Note that the redox potentials are written as reduction potentials, even for the oxidation reactions.]

Chlorine dioxide can be oxidized and reduced to many other species in addition to the two illustrative reactions depicted above. Thus, exposure of chlorine dioxide to strong oxidizing agents will result in the oxidation of the chlorine dioxide, and prevent it from reaching the sensor.

Another type of filter commonly used to protect gas sensors from exposure to hydrogen sulfide uses a metal salt which forms an insoluble sulfide. One of the most commonly used metal salts is lead acetate, which forms the black product, lead sulfide, upon exposure to hydrogen sulfide.

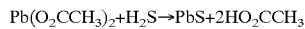

Blurton et al in U.S. Pat. Nos. 4,001,103, 4,052,268 and 4,127,462 describe the use of lead acetate and mercuric chloride filters to protect nitrogen dioxide and nitric oxide electrochemical sensors from hydrogen sulfide. Similarly, Stahl et al have described the use of some silver salts for preventing the cross sensitivity of hydrogen sulfide on sulfur dioxide sensors in U.S. Pat. No. 4,127,386.

Exposure of aqueous solutions of many transition metal ions to hydrogen sulfide results in the precipitation of the darkly colored metal sulfides. These reactions are well known in analytical chemistry and are used as a means of identifying the metal ions, as well as a test for hydrogen sulfide in spot tests and gas detection tubes ("Inorganic Reactions at Advanced Level", D. G. Davies, T. V. G. Kelly, Mills & Boon Ltd., London, 1977; "Spot Tests", F. Feigl, Vol. 1, Elsevier Publishing Company, Amsterdam, 1954; "Drager-Tube Handbook", 8$^{th}$ Edition, National Draeger Inc., Pittsburgh, Pa.). Silver nitrate, for example, has been used to measure hydrogen sulfide concentration in atmospheric studies using impregnated paper tape ("Hydrogen sulfide in the atmosphere of the northern equatorial Atlantic ocean and its relation to the global sulfur cycle," B. J. Slatt, D. F. S. Natusch, J. M. Prospero, D. L. Savoie, Atmos. Environ. (1978), 12 (5), 981–991; "Determination of hydrogen sulfide in air: an assessment of impregnated paper tape methods", D. F. S. Natusch, J. R. Sewell, R. L. Tanner, Analytical Chemistry, (1974), 46 (3), 410–415). A more complete discussion of the reactions of hydrogen sulfide with transition metals can be found in standard texts ("Inorganic Chemistry," P. C. L. Thorne, E. P. Roberts, Interscience Publishers Inc., New York, 1948).

The use of filters containing lead, mercury and other transition metals to prevent the cross sensitivity of hydrogen sulfide on gas sensors is well known in the prior art, as is illustrated by the patents of Blurton et al described above. This type of filter usually works very well for many types of sensors and other applications where it is necessary to remove hydrogen sulfide gas. Lead sulfide filters have even been used in prior art sensors for chlorine dioxide, though their use in this application has severe drawbacks.

Chlorine dioxide does not react with lead acetate to a significant extent, and thus passes through a lead acetate impregnated filter placed in the gas diffusion path of the sensor. Hydrogen sulfide reacts with lead acetate to form lead sulfide and thus the hydrogen sulfide is unable to reach a sensor protected by a lead acetate impregnated filter. However, it has been found that this lead sulfide formed by the reaction of the hydrogen sulfide with the lead acetate reacts readily with chlorine dioxide, so if a sensor protected by a lead acetate impregnated filter is sequentially exposed to test gases containing chlorine dioxide, then hydrogen sulfide and then chlorine dioxide again, the response of the sensor to the second exposure to chlorine dioxide is greatly reduced compared to the response to the first exposure to chlorine dioxide.

This particular problem is especially insidious since a sensor protected with a metal acetate filter may respond well to chlorine dioxide prior to exposure to hydrogen sulfide. There may be no indication of exposure to hydrogen sulfide, since the filter is effective at removing that gas, but subsequent to the exposure of hydrogen sulfide, the filter will greatly reduce the amount of chlorine dioxide reaching the sensor. Alternatively, in an environment such as a paper mill where exposure to low levels of hydrogen sulfide (below permissible exposure limits) is common, a gradual loss in response to chlorine dioxide may occur, and the instrument may fail to provide a warning to personnel in the event of a dangerous chlorine dioxide atmosphere. The hydrogen sulfide exposure need not be at the same time as a the chlorine dioxide exposure; instead it may have occurred at an earlier time, or even another day.

Clearly, there is a need for a filter that is suitable for use with an electrochemical gas sensor which will prevent hydrogen sulfide from reaching the sensor, and which will allow chlorine dioxide to reach the gas sensor both prior to and subsequent to exposure to hydrogen sulfide.

SUMMARY OF THE INVENTION

It is therefore an object of the invention to provide a filter for use with electrochemical chlorine dioxide sensors for removal of hydrogen sulfide without affecting passage of chlorine dioxide.

It is a further object of the invention to provide a filter for use with electrochemical chlorine dioxide sensors for removal of hydrogen sulfide which does not result in false positive or false negative indications of chlorine dioxide after exposure to hydrogen sulfide.

It is still another object of the invention to provide an improved method for electrochemical detection of chlorine dioxide by completely removing hydrogen sulfide from the gaseous medium being tested.

To achieve these and other objects, the invention provides a filter for removal of hydrogen sulfide from a gaseous medium to be tested for chlorine dioxide by an electrochemical sensor comprising a filter substrate impregnated with a reagent which is a copper (II) salt or a silver (I) salt which reacts with hydrogen sulfide in a reaction which does not produce an oxidizing or reducing gas. Such filters have been found to be extremely efficient in the removal of hydrogen sulfide but do not affect passage of chlorine dioxide.

DETAILED DESCRIPTION OF THE INVENTION

Figure 1:
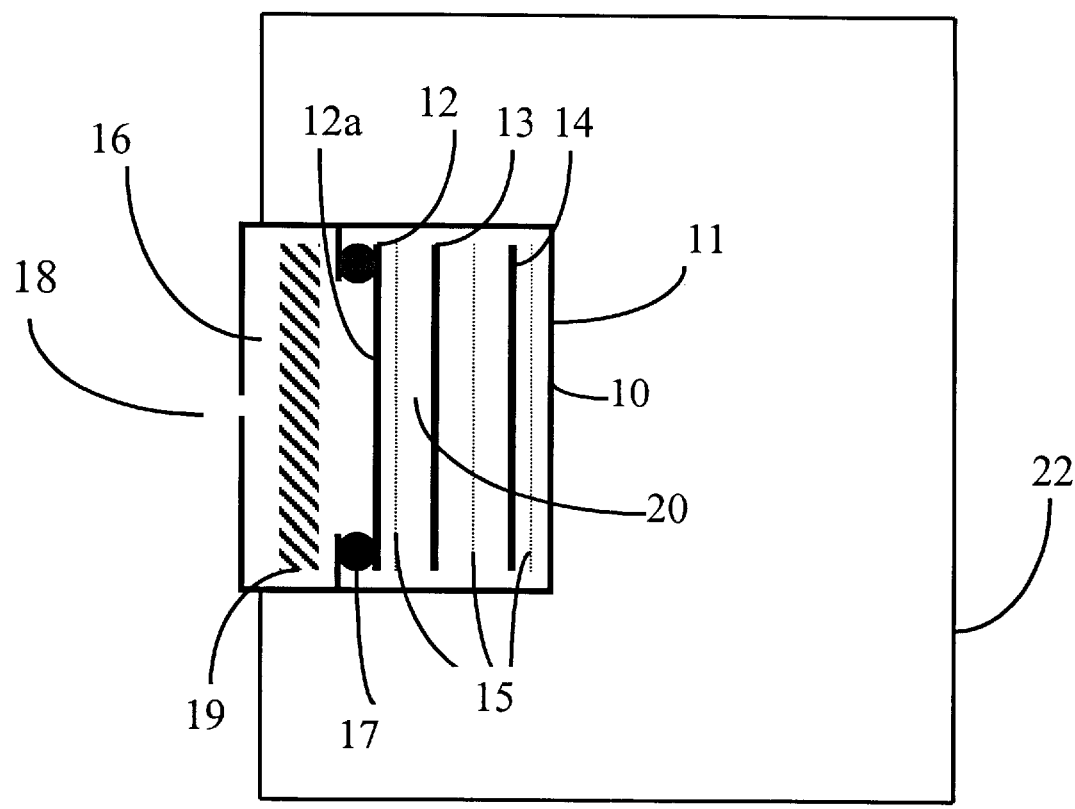
FIG. 1 is a cross-sectional diagram of an electrochemical sensor apparatus showing a filter operating in a diffusion mode.

The filter of the invention comprises a reagent impregnated in a filter substrate or support.

The reagent is selected from among those chemical compounds which will react with hydrogen sulfide present as an impurity in a gaseous medium and thus remove the hydrogen sulfide from the gaseous medium without additional contamination. The reaction should occur at a rate, given the dimensions of the filter and the amount of hydrogen sulfide in the gas, such that substantially no hydrogen sulfide passes through the filter to reach the chlorine dioxide sensor. Furthermore, the reagent and the filter substrate should be substantially non-reactive with chlorine dioxide to allow chlorine dioxide to pass through the filter essentially unchanged in concentration.

Compounds which have been found to meet these requirements include salts of silver in oxidation state +1 and salts of copper in oxidation state +2, with the preferred compounds being copper chloride ($CuCl_2$), copper bromide ($CuBr_2$), silver acetate ($AgO_2CCH_3$), silver bromate ($AgBrO_3$), silver bromide (AgBr), silver carbonate ($Ag_2CO_3$), silver chloride (AgCl), silver chromate ($Ag_2CrO_4$), silver cyanide (AgCN), silver iodate ($AgIO_3$), silver oxide ($Ag_2O$), silver perchlorate ($AgClO_4$), silver permanganate ($AgMnO_4$), silver sulfate ($Ag_2SO_4$), silver hexafluorophosphate ($AgPF_6$), silver fluoride (AgF), silver tetrafluoroborate ($AgBF_4$), silver iodide (AgI) and silver trifluoromethane sulfonate ($AgO_3SCF_3$).

Nitrates of silver and copper have been found to be unsuitable for the purposes of the invention. When filters containing these nitrates are exposed to hydrogen sulfide, the sensor shows a positive response relative to chlorine dioxide, indicating the presence of an easily reduced gas. Applicants believe that the reaction of hydrogen sulfide with copper or silver nitrate produces nitrogen dioxide, a strong oxidizing agent. Copper and silver nitrate should therefore be avoided for the purposes of the invention, as should other reagents which react with hydrogen sulfide to form oxidizing or reducing gases.

The use of a silver reagent to remove hydrogen sulfide from gas streams being analyzed for sulfur dioxide monitor was disclosed by Stahl et al in U.S. Pat. No. 4,127,386, in which an inline filter for a sample draw sulfur dioxide analyzer included a tube filled with the crystals of a silver salt, specifically silver sulfate, silver nitrate or silver iodide. Silver sulfate was most preferred. The silver salts removed the hydrogen sulfide but allowed the sulfur dioxide to pass through. Stahl et al found that the efficacy of the filter depended greatly on the silver salt selected and other commonly available silver salts were found to be far less effective.

The support for the filter of the invention may be made of any material that can retain the reagents in a high surface area form, and still allow gases to readily pass through the filter. The filter support also needs to be chemically compatible with the reagents and with chlorine dioxide. It is also advantageous if the filter support is wet by the reagent solution, since this facilitates deposition of the reagent on the support. In the prior art, filter supports for gas sensors have been made of porous media, such as filter paper, glass fiber mats or small particles, both porous and non-porous, which are coated with the reagents. The preferred medium for a filter support is a glass fiber mat, which combines high surface area, porous structure, and ease of handling; glass fiber filter disks such as those available from Whatman Inc. and Fisher Scientific Corporation are typical. However the use of other filter support media is well known in the art and may be readily used with this invention. In particular, the filter support may also be a particulate solid, an ion exchange particulate solid or a porous membrane.

If the filter is being used as an in-line filter, such that the gas is flowing through the filter material, then the filter needs to be constructed of a suitable material which presents a high surface area to the filter, but which does not present too much back pressure. If the back pressure is too high, then there is potential for inefficiency and strain on the pump, and increased risk of leaks around the filter or tears forming in the filter material. The physical strength requirements of an in-line filter are greater than those wherein the gas passes through by diffusion, since an in-line filter must be able to withstand a pressure drop.

If the filter material is placed in front of the sensor or in the sensor, such that the gas passes through the filter by natural diffusion, then the filter medium needs to be selected so that the filter does not present an excessive diffusion barrier to the gas. Even a porous filter will present a diffusion barrier to the gases reaching the sensor, and the greater the diffusion barrier, the greater the reduction in the sensitivity of the sensor. Furthermore, a larger diffusion barrier due to the filter will result in a longer response time from the sensor.

The amount of gas which is required to flow through the filter will depend on the instrument design, but the size of the filter and the capacity of the filter will have to be selected to meet the expected demand for hydrogen sulfide removal. Thus, a filter designed for an application where a sensor may occasionally see 1–2 ppm hydrogen sulfide may differ from an application where there is a constant 15 ppm background gas. Similarly, a filter which is located behind a diffusion barrier within a sensor will require less capacity (or will last longer) than a similar filter in front of the sensor. If insufficient reagent is deposited on the filter support, then the filter will fail to remove all of the hydrogen sulfide, or it will have a limited capacity to remove hydrogen sulfide.

In a preferred embodiment, an absorbent fiber disc or more preferably a glass fiber disc has a chemical reagent for the removal of the hydrogen sulfide coated on its surface or absorbed into its bulk. This operation is conveniently performed by adding a solution of the reagent in a suitable solvent to the substrate, and mixing as necessary to ensure an even coating or absorption, and allowing sufficient time for the solvent to evaporate. The preferred solvent is water, though other solvents may also be used, depending on the solubility and chemical properties of the reagent used.

If the desired reagent is not readily soluble in water or other solvent, then the filter can be prepared by an alternative method. The reagent may be prepared on or in the substrate or both, by the addition of two reagent solutions which react to produce the desired insoluble reagent. Wor example, if the desired reagent is silver acetate ($AgO_2CCH_3$), which is essentially insoluble in water, the substrate may be treated with water solutions of silver tetrafluorborate ($AgBF_4$) and sodium acetate ($NaO_2CCH_3$), and insoluble silver acetate is produced in and on the substrate by their reaction.

If the filter is prepared by adding a single solution of the reagent in a solvent, preferably water, to the filter support, then the amount of reagent that can be added to the filter disk will be limited by the solubility of the reagent in the solvent and by the absorbance capacity of the filter support for the solution. Addition of more solution after the solvent of the first solution has evaporated can increase the loading of the reagent on the filter support if needed.

If excess reagent is added to the filter, such that the reagent cakes or crystallizes on the surface, then the reagent at the center of the cake will be inaccessible to the gas and so will be wasted, and silver salts are relatively expensive. Furthermore, if the reagent is present in sufficient excess to block the gas path through the filter support, then the gas flow rate or gas diffusion rate through the filter will be reduced excessively, and the response of the sensor will be compromised. Therefore the amount of reagent added to the filter should be sufficient to give a high hydrogen sulfide removal capability, but beyond this point, additional reagent will not be an advantage.

The optimum amount of reagent on and in the filter will depend on the surface area of the support and the crystal morphology of the reagent on the support (e.g. a few big crystals vs. many little ones), among other factors. It is not practical and probably not possible to predict the optimum loading from a theoretical or stoichiometric stand point with any reliability; the optimum leading is far better determined experimentally. Thus, a predetermined loading is applied to a filter which is then tested with a known concentration of hydrogen sulfide, and the time before the gas starts to pass through the filter, the amount of hydrogen sulfide removed and the filter capacity are determined.

A typical electrochemical sensor 10 is shown in FIG. 1. The sensor comprises a sensor body 11, containing three electrodes in sequence, a working electrode 12, a reference electrode 13 and a counter electrode 14. The three electrodes 12, 13 and 14 are separated by inert media 15, soaked in electrolyte. Typically this inert media 15 comprises glass paper, and the electrolyte may be an aqueous or non-aqueous solution of a salt which provides ionic electrical conductivity between the electrodes 12, 13 and 14. Electrode 12 and an O-ring seal 17 divide the sensor 10 into a gas volume portion 16 and an electrode compartment 20. The electrolyte is retained within the electrode compartment 20 by the compression of an O-ring seal 17 against rear side 12a of electrode 12.

The gas to be detected diffuses into the sensor 10 through gas entry hole 18 into gas volume 16. Within this volume 16 is a chemical filter 19, designed to remove one or more interfering components of the gas. The gas diffuses through the chemical filter 19, to the back side 12a of the working electrode 12. The working electrode 12 is typically comprised of a porous membrane with a precious metal (not shown) fixed onto the inner surface of the membrane comprising electrode 12.

The sensor 10 is encased in a housing 22 which may include circuitry for control and operation of the sensor and display of the output readings, or which may connect to control, operation and display circuitry at a remote location. By making the sensor accessible, the filter can be easily replaced when exposure to hydrogen sulfide has exhausted the reagent, or the entire sensor can be easily replaced when necessary.

This sensor is a typical one which has been described for illustrative purposes only and many variations on electrochemical sensor design are known in the art. Further details of electrochemical sensor operation and design may be found in the following references: S. C. Chang, J. P. Stetter, C. S. Cha, "Amperometric Gas Sensors", Talanta (1993), 40 (4) 461–477; B. S. Hobbs, A. D. S. Tantram, R. Chan-Henry, "Techniques and Mechanisms in Gas Sensing", Ed. P. T. Moseley, J. O. W. Norris and D. E. Williams, Adam Hilger, Bristol, 1991.

Figure 2:
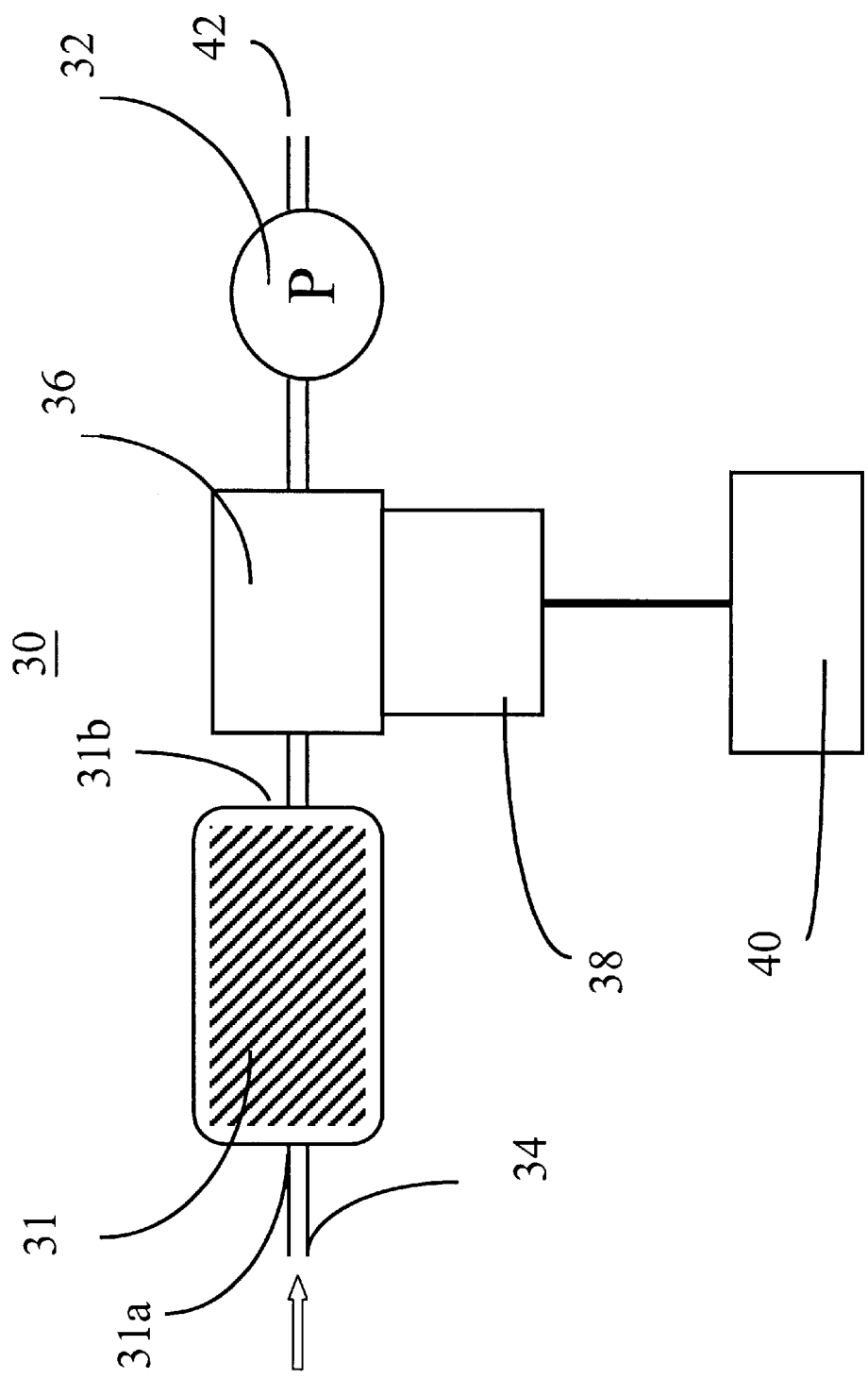
FIG. 2 is a schematic diagram of an electrochemical sensor apparatus with a filter operating in an in-line mode.

FIG. 2 shows a sensor apparatus 30 operating in an in-line mode, with gas passing through filter 31 from inlet 31a to outlet 31b. Gas flow is driven by a pump 32 which creates suction at inlet 31a, with gas flowing through line 34. From the filter 31, gas passes into a manifold 36, which exposes an electrochemical sensor 38 to the gas. The sensor 38 is operated by circuitry 40 to which it is connected, either locally or at a remote location. Excess gas exits at pump outlet 42.

EXAMPLE

1. Preparation of a Reagent Filter

Nine cm diameter glass fiber disks were obtained for preparation of filters. A first disk was placed horizontally on an inert support, and a solution of silver hexafluorophosphate (0.5 g) in water (1.2 ml) was applied to the glass fiber disk with a pipette evenly across the surface. The impregnated glass fiber disk was allowed to dry overnight, before filter disks were cut out of impregnated filter with a punch. The diameter of the disk was selected to match the diameter of the gas path into the sensor.

A second filter was left untreated, while other filters were treated with lead acetate and other compounds including silver fluoride, silver tetrafluoborate, copper chloride. copper nitrate, silver nitrate, cobalt nitrate and sodium nitrate.

2. Comparative Testing of Filters

The filters prepared as described above were placed in front of a chlorine daoxide sensor (Sensoric GmbH, Bonn, Germany) which had its internal filters removed for test purposes. The sensor was connected to a conventional potentiostat controller and the output was recorded on an X-Y chart recorder.

For test purposes, The sensor was exposed to about 0.7 ppm chlorine dioxide produced by an electrochemical gas generator (Advanced Calibration Designs, Tucson, Ariz.) for several minutes, followed by 50 ppm hydrogen sulfide in nitrogen from a compressed gas cylinder, followed by a second exposure to chlorine dioxide.

When a control filter was used (filter support without any reagent), the sensor gave a strong signal to chlorine dioxide when exposed to chlorine dioxide and a strong negative signal (relative to the response to chlorine dioxide) when the sensor was exposed to hydrogen sulfide. On subsequent exposure of chlorine dioxide to the sensor, the sensor again gave a positive response.

When the filter impregnated with lead acetate was placed in front of the sensor, exposure of the sensor to chlorine dioxide produced a strong response, similar to that seen with the control filter, described above. When hydrogen sulfide gas was applied to the sensor, there was essentially no response from the sensor. Thus, this conventional lead acetate impregnated filter was working well to remove hydrogen sulfide from the gas and prevent hydrogen sulfide from reaching the sensor. However, when the sensor was again exposed to chlorine dioxide, there was essentially no response from the sensor for a period of at least ten minutes. The chlorine dioxide was reacting with the lead sulfide formed on the filter by the prior exposure of the filter to hydrogen sulfide, and the chlorine dioxide was not reaching the sensor electrode.

When the filter impregnated with silver hexafluorophosphate was placed in front of the sensor and the sensor was exposed to chlorine dioxide, there was a strong response from the sensor. When the sensor was exposed to hydrogen sulfide, there was essentially no response from the sensor, indicating that the silver hexafluorophosphate-impregnated filter was removing the hydrogen sulfide from the gas diffusing to the sensor. When the sensor was subsequently re-exposed to chlorine dioxide, the sensor again gave a strong response, indicating that even though the filter had been exposed to hydrogen sulfide, chlorine dioxide could still pass through the filter. The response of the sensor to chlorine dioxide subsequent to the exposure to hydrogen sulfide was similar in magnitude to the response of the sensor to chlorine dioxide prior to the exposure to hydrogen sulfide.

A similar result was obtained with other silver salts, including silver fluoride and silver tetrafluoroborate, and with copper salts, such as copper (II) chloride. From these results it appears that the salts of metals from Group IB of the periodic table function to remove hydrogen sulfide.

However, when a silver nitrate impregnated filter was tested, it was found that when upon exposure to hydrogen sulfide, the sensor gave a positive response relative to chlorine dioxide. The reaction of chlorine dioxide in the electrochemical sensor is a reduction reaction, as described above. Therefore, a positive signal upon exposing a sensor protected by a silver nitrate impregnated filter indicates the presence of an easily reduced gas. There are relatively few gases which are easily reduced, and the most likely candidate is nitrogen dioxide ($NO_2$). It is well known that nitrogen dioxide can be produced by the reduction of nitrates, and it is hypothesized that the hydrogen sulfide reacts with the silver nitrate in the filter to produce a small amount of nitrogen dioxide. When copper nitrate was tested, a similar result was obtained. Again, it is hypothesized that the hydrogen sulfide reacts with the copper nitrate filter to produce a small amount of nitrogen dioxide. however, when sodium nitrate, cobalt nitrate and ferrous nitrate impregnated filters were similarly tested, there was no indication of a reducing gas. It is believed that this difference is due to the catalytic nature of the copper and silver.

It is well known in the prior art that aqueous solutions of many silver salts and copper salts will react with hydrogen sulfide to form silver or copper sulfide, respectively. While it is not desired that the invention be restricted to a particular theory of operation, it is believed that this reaction occurs in the filter media containing silver and copper salts upon exposure to hydrogen sulfide gas. It is further believed that the main difference between the efficacy of silver and copper salt impregnated filters and lead acetate impregnated filters is due to the less reactive nature of the metal sulfide salt produced.

The invention herein has been described for use as a filter in the gas path within a three-electrode electrochemical gas sensor, as depicted in the Figure. This configuration is intended to be exemplary only, and it is not intended to limit the scope of this invention which may be used without restriction for gas sensors other than a three-electrode gas sensor, including electrochemical sensors with two electrodes, or sensors based on other sensor technologies, such as those based on spectroscopic methods.

The filter of this present invention does need to be in the gas path to the sensor, and any position of the filter which meets this requirement is within the scope of this invention. For example, the filter may be located outside of the sensor, or in a gas detection system wherein the analyte gas is drawn or pumped down a tube, the filter of the invention may be employed as an inline filter. Similarly, this invention may be applied to sensors which detect chlorine dioxide by the natural diffusion of the gas molecules into the sensors, or the gas sample may be delivered to the sensor via a pump. Other methods of delivering the analyte gas to the sensing element of the gas detection device are within the scope of this invention.

While the preferred embodiments of the invention have been shown and described, it will be apparent to those skilled in the art that changes can be made in the embodiments without departing from the spirit and principles of the invention.

What is claimed is:

1. A method for specifically detecting chlorine dioxide in a gaseous medium comprising the steps of:
    a) passing gaseous medium to be tested through a filter comprising a filter substrate impregnated with a solid reagent which is a silver I or copper II salt which reacts with hydrogen sulfide without producing an oxidizing or reducing gas, to thereby substantially remove hydrogen sulfide from the gaseous medium; and
    b) passing the gaseous medium from which hydrogen sulfide has been substantially removed to a means for specifically detecting chlorine dioxide, and detecting any chlorine dioxide present in the gaseous medium.

2. The method of claim 1, wherein the reagent is selected from the group consisting of cupric chloride, cupric bromide, silver acetate, silver bromate, silver bromide, silver carbonate, silver chloride, silver chromate, silver cyanide, silver iodate, silver oxide, silver perchlorate, silver permanganate, silver sulfate, silver iodide, silver hexafluorophosphate, silver fluoride, silver trifluoromethane sulfonate, silver tetrafluoroborate and mixtures thereof.

3. The method of claim 1, wherein the filter substrate comprises glass fibers.

4. An apparatus for the detection of chlorine dioxide in a gaseous medium comprising a specific detector for chlorine dioxide placed in a path for the gaseous medium, and a filter for removal of hydrogen sulfide from the gaseous medium placed in the path for the gaseous medium upstream of the detector, the filter comprising a filter substrate impregnated with a reagent which is a solid silver I or copper II salt which reacts with hydrogen sulfide without producing an oxidizing or reducing gas, and which thereby substantially removes hydrogen sulfide from the gaseous medium.

5. The apparatus of claim 4, wherein the reagent is selected from the group consisting of cupric chloride, cupric bromide, silver acetate, silver bromate, silver bromide, silver carbonate, silver chloride, silver chromate, silver cyanide, silver iodate, silver oxide, silver perchlorate, silver permanganate, silver sulfate, silver iodide, silver hexafluorophosphate, silver fluoride, silver trifluoromethane sulfonate, silver tetrafluoroborate and mixtures thereof.

6. The apparatus of claim 4, wherein the filter substrate comprises glass fibers.

7. The apparatus of claim 4, wherein the detector and filter are disposed in a single housing.

8. The apparatus of claim 4, wherein the detector is disposed in a housing separate from the filter.

9. The apparatus of claim 4, wherein the detector is an electrochemical detector.

10. The apparatus of claim 7, wherein the detector is an electrochemical detector and the housing is divided into a portion containing electrodes and an electrolyte, and a gas volume portion containing the filter.

11. The apparatus of claim 4, wherein the filter operates in a diffusion mode.

12. The apparatus of claim 4, wherein the filter operates in an in-line mode, and includes a gas inlet and gas outlet.

13. The apparatus of claim 12, additionally comprising a gas manifold connected to the filter outlet and to a pump for creating a filtered gas flow through the manifold, the manifold being in flow communication with the detect-or for chlorine dioxide.

* * * * *